US006635267B1

(12) United States Patent
Miyoshi et al.

(10) Patent No.: US 6,635,267 B1
(45) Date of Patent: *Oct. 21, 2003

(54) HYALURONIC ACID GEL, PROCESS FOR THE PREPARATION THEREOF AND MEDICAL MATERIALS CONTAINING THE SAME

(75) Inventors: Teruzou Miyoshi, Tokyo (JP); Hironoshin Kitagawa, Tokyo (JP); Kazuhiko Arai, Niigata (JP); Hiroshi Kaneko, Tokyo (JP); Toshihiko Umeda, Tokyo (JP)

(73) Assignee: Denki Kagaku Kogyo Kabushiki Kaisha, Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 09/831,343

(22) PCT Filed: Nov. 9, 1999

(86) PCT No.: PCT/JP99/06232

§ 371 (c)(1),
(2), (4) Date: May 10, 2001

(87) PCT Pub. No.: WO00/27405

PCT Pub. Date: May 18, 2000

(30) Foreign Application Priority Data

| Nov. 10, 1998 | (JP) | 10/318969 |
| Jan. 12, 1999 | (JP) | 11/005424 |
| Jan. 27, 1999 | (JP) | 11/018017 |
| Feb. 12, 1999 | (JP) | 11/033974 |
| Feb. 19, 1999 | (JP) | 11/042372 |

(51) Int. Cl.⁷ .............................................. A61F 13/00
(52) U.S. Cl. .................. 424/422; 424/423; 424/426; 424/484; 424/485; 424/78.08; 424/78.17; 514/54
(58) Field of Search ................ 424/422, 423, 424/426, 78.08, 78.17, 484, 485; 514/54, 944, 825, 912

(56) References Cited

U.S. PATENT DOCUMENTS

| 4,716,154 A | 12/1987 | Mälson et al. ............... 514/54 |
| 5,432,167 A | 7/1995 | Brismar ........................ 514/54 |
| 5,783,691 A * | 7/1998 | Malson et al. .............. 536/55.1 |
| 6,387,413 B1 * | 5/2002 | Miyata et al. ............... 424/548 |
| 2002/0098244 A1 * | 7/2002 | Miyata et al. | |

FOREIGN PATENT DOCUMENTS

| EP | 0 291 177 | 11/1988 |
| EP | 0 718 312 | 6/1996 |
| EP | 1 005 874 | 6/2000 |
| JP | 5-58881 | 3/1993 |
| WO | WO 90/09401 | 8/1990 |
| WO | WO 96/33751 | 10/1996 |
| WO | WO 97/49412 | * 12/1997 |

OTHER PUBLICATIONS

J. G. Peyron, Database MEDLINE Online National Library of Medicine, AN. NLM8410878, XP–002194145, 1 page, "Intraarticular Hyaluronan Injections in the Treatment of Osteoarthritis: State–of–the–Art Review", 1993.

N. E. Larsen, et al., Journal of Biomedical Materials Research, vol. 25, No. 6, XP–002191764, pps. 699–710, "Hylan Gel Composition for Percutaneous Embolization", 1991 (pp. 707 and 708 will be filed later).

R. C. Pruett, et al., Database MEDLINE Online US National Library of Medicine, AN. NLM518384, XP–002194146, 1 page, "Hyaluronic Acid Vitreous Substitute. A Six–Year Clinical Evaluation", 1979.

N.E. Larsen, et al., Journal of Biomedical Materials Research, vol. 25, No. 6, XP–002191764, pps. 699–710, "Hylan Gel Composition for Percutaneous Embolization", 1991.

* cited by examiner

Primary Examiner—Thurman K. Page
Assistant Examiner—Liliana Di Nola-Baron
(74) Attorney, Agent, or Firm—Oblon, Spivak, McClelland, Maier & Neustadt, P.C.

(57) ABSTRACT

A gel made of hyaluronic acid alone which is hardly soluble in a neutral aqueous solution and has fluidity enough to be easily ejectable from an injector.

16 Claims, No Drawings

HYALURONIC ACID GEL, PROCESS FOR THE PREPARATION THEREOF AND MEDICAL MATERIALS CONTAINING THE SAME

TECHNICAL FIELD

The present invention relates to a novel hyaluronic acid gel with fluidity or with fluidity and transparency and a method of its production, and further, to a biomedical material with good biocompatibility.

BACKGROUND ART

Hyaluronic acid (hereinafter referred to simply as HA) is a linear macromolecular polysaccharide consisting of alternately bonded β-D-N-acetylglucosamine and β-D-glucuronic acid. HA is found not only in connective tissues of mammals but also in cockscombs and the capsules of Streptococci. HA is obtainable not only by extraction from cockscombs and umbilical cords, but also as purified products from the culture broth of streptococci.

Natural HA is polydisperse in respect of molecular weight and is known to show excellent biocompatibility even when implanted or injected into the body by virtue of the absence of species and organ specificity. However, because of the relatively short in vivo residence time of HA solution in biological application, improvement of the persistency of HA by chemical crosslinking with various chemical modifiers has been attempted to broaden its use for medical materials.

(I) Concerning the joints, synovial fluid supplies nutrition to the articular cartilage and has incomparable functions as a lubricant and a shock absorber. It is clarified that its excellent viscoelastisity heavily owes to one of the main components, HA.

Concentration and molecular weight analyses of HA demonstrated the concentration and molecular weight of HA in the synovial fluid from patients with arthritis such as osteoarthritis and chronic articular rheumatism generally tended to lower than in normal synovial fluid, and the lower concentration and molecular weight of HA were closely associated with development of locomotor dysfunction and pain attributable to the weaker lubricating action and the weaker protecting action on the surface of the articular cartilage of synovial fluid.

Injection of high molecular weight HA solution (Artz: from Seikagaku Corporation, average molecular weight 900000; Hyalgan: from Fidia, average molecular weight <500000) into diseased joints has been widely adopted as an effective measure for osteoarthritis among those articular diseases, and the source of high purity HA preparations for this purpose is cockscombs. Such HA preparations from cockscombs are biologically inherent and quite safe but usually have to be administered as frequently as several to 10 times to show significant therapeutic effect.

Persistency tests on rabbits revealed that HA with a molecular weight of less than 1000000 administered into the knee joint cavities disappeared from the knee joint cavities in 1 to 3 days and suggested the need of frequent administrations (Blood Coagulation and Fibrinolysis, vol 12, 173, 1992).

On the other hand, the molecular weight of HA found in the living body is reported to be as high as millions to 10000000, and a crosslinked HA derivative [Hylan: from Biomatrix] obtained by treatment with a chemical crosslinker has been developed as a therapeutic agent for knee joints with the idea that high molecular weight HA closer to the biologically intact one is likely to have higher effect.

Reportedly, the crosslinked HA persisted for a period as long as 20 to 30 days after administration into rabbit knee joint cavities in the above-mentioned persistency tests and produced sufficient effect when administered three times in clinical tests, and is practically used as a therapeutic agent for arthritis (Journal of Theumatology vol.20, 16, 1993).

(II) Next, concerning emboli, treatments through embolization are known to effective for various diseases such as angiopathy, paraplastic aneurysm and varix. Obstruction of arteries as the nourishing channels for tumours is also effective in tumour treatment.

Some proposals have been made for embolization. For example, a balloon embolization method using a balloon-tip catheter has been developed (W. Taki et al., Surg. Neurol, Vol.12, 363, 1979). In addition, a method in which 2-hydroxyethyl methacrylate (HEMA) is introduced into a balloon together with a polymerization catalyst through a catheter is also known (W. Taki et al., Surg. Neurol, Vol.13, 140, 1980).

For cancer treatment through embolization, use of cisplatin-containing chitin (Tahara et al., Cancer and Chemotherapy, vol.21(13), 2225, 1994), use of poly(benzyl 1-glutamate) microspheres carrying cisplatin (Li C et al., Parm, Res., Vol.11(12), 1792, 1994) and use of SMANCS and Lipiodol suspension together with gelatin sponge as a embolizing material (Nakamura et al., Cancer and Chemotherapy, vol.22(11), 1390, 1996) have been reported. In addition, Poly(DL-lactate) microspheres are reported as a suitable material for use in embolismic chemotherapy in combination with continuous injection of a chemotherapeutic agent (Flandroy P et al., J Control Release, Vol.44(2/3), 153, 1997) while it is mentioned that they have to biodegrade in a couple of days so that when this therapy is practiced repeatedly.

There are a lot of problems such as the short time obstruction in the balloon embolization due to shriveling of the balloon as a bar to production of satisfactory effect and the possibility of polymerization of monomers such as HEMA inside the catheter. Most embolizing materials used in embolismic chemotherapy are synthetically available and hardly biodegradable and doubtful in respect of biocompatibility. Poly(DL-lactate) microspheres, though biodegradable, do not guarantee complete safety when repeatedly administered.

Though highly biocompatible HA has no problem with safety, HA does not embolize when merely administered in the form of solution, and is required to have improved local persistency.

(III) Concerning soft tissues, the idea of injecting various materials to repair or swell soft tissues has rapidly developed since the invention of the subcutaneous injection needle, and a number of materials have been injected into human bodies to remedy soft tissues and skins. Among them, liquid silicone has been used widely for injection but is not used as much recently as it used to be due to its side effects such as skin ulceration attributable to its long retention time. Collagen has also been injected so far in various forms such as chemically crosslinked forms and fibrous forms. Crosslinked solid collagen requires incision to be injected and has problems plasticity and flexibility. There is a disclosure about fibrous collagen in U.S. Pat. No. 3949073.

However, it shrinks in volume as its liquid components are absorbed and has to be supplemented. Injectable types of collagen like this can hardly be freed of contaminants such as immunity substances, are costly and do not necessarily have appropriate physical properties.

HA has also been attempted as an injection for soft tissues (Ann. Plast. Surg., Vol.38, 308, 1997). Because HA in solution is rapidly absorbed in vivo, various methods for chemical crosslinking of HA have been attempted to improve persistency and retention in soft tissues (U.S. Pat. No. 4582865, JP-B-6-37575, JP-A-7-97401, JP-A-60-130601).

And hylan B gel is commercially available as Hylaform in Europe (The Chemistry Biology and Medical Application of Hyaluronan and its Derivatives Vol.72, p278, PORTLAND PRESS).

(IV) Next, reference will be made to the posterior part of the eyeball, especially the retina bordered on the vitreous body. The retina marks the posterior boundary of the intraocular space, while the lens and the ciliary body mark the anterior boundary. The retina consists of two layers, the receptor layer of photosensitive cells in contact with the vitreous humor and the layer of pigment epithelial cells adjacent to the choroid. Liquid infusion into the receptor layer causes retinal detachment, separating the two layers of the retina.

For treatment of retinal detachment, the peeled retina is brought into contact with the pigmented epithelial layer and fastened by photocoagulation or cryocoagulation. The contact is achieved by pressing a inward buckle against the sclera and the choroids from outside or by generating pressure from vitreous humor onto the retina through volume expansion of vitreous humor by injection.

In the latter case, because vitreous humor has to be removed partly or completely due to too much spilt blood for reabsorption or inward growth of the retina accompanying retinal detachment, various materials have been attempted as artificial vitreous bodies.

These artificial vitreous bodies are intended to maintain the shape of the eyeball and bring back the retina in position while pressing the retina against the pigmented epithelium in the vitreous chamber.

As artificial vitreous bodies, physiological saline, glycerin, animal vitreous bodies, air, various gases, polyvinyl alcohol, collagen gel, silicone oil, HA and perfluorocarbons may be mentioned, and air, gases such as sulfur hexafluoride, silicone oil, liquid perfluorocarbons such as perfluorooctane and perfluorodecalin are generally used now.

Various expansive gases are used as artificial vitreous bodies by themselves or in mixtures with air, and have proven to be useful (American Journal of ophthalmology, Vol.98, 180, 1984).

However, they sometimes cause complications such as increase of intraocular pressure and coreclisis attributable to gas expansion or keratoleukoma attributable to their contact with the corneal endothelium and impose on patients a heavy burden of keeping their faces down for a long time.

Silicone oil maintains the intraocular space for a longer time than gases by virtue of its little absorbability and accelerates adhesion of the retina effectively (Retina, Vol.7, 180, 1987), but is used with the proviso that it is drawn out after exertion of the pressing effect on the retina. Further, it is said to have serious problems of cataract, glaucoma and toxic effects on the ocular tissue (Ophthalmology, Vol.27, 1081, 1985).

Liquid perfluorocarbons as artificial vitreous bodies are proved to cause complications such as proliferative vitreoretinopathy, cataract and intraocular hypotension and are reported to be more questionable than silicone oil and gases in respect of safety and effectiveness (New Ophthalmology, Vol.12, 1053, 1995).

HA has been investigated a lot since Balazs reported its application in the field of ophthalmology (Mod. Probl. Ophthalmol., Vol.10, 3 1972) and is widely used in ophthalmic surgery, especially intraocular implantation.

HA is inherently biogenic and never induces toxic or immunological reactions. However, HA can not exert the effect of maintaining the intraocular space for a long time sufficient for treatment of serious retinal detachment because HA injected into the vitreous chamber dissolves in aqueous humor and is discharged from the eye through the anterior chamber and the fibrous trabecular goniomeshwork without being decomposed.

Though vitreous injections containing HA, for example, which contain at least 1.5 wt %, preferably from 2 to 2.5 wt % of HA with a molecular weight of at least 900000, preferably 1600000 to 2000000 are disclosed in JP-A-5-184663, they are not retained in the intraocular space {Nippon Ganka Kiyou, vol.38, 927, 1987}. Additionally, over 1 wt % solution of HA with such a molecular weight strains a syringe when ejected from the syringe into the vitreous body and is not practical.

As mentioned above, improvement of the in vivo retention of HA is essential for its applications, and various chemical crosslinkers have been used to crosslink HA (U.S. Pat. No. 4582865, JP-A-60-13060, JP-A-63-28166, JP-B-6-37575, JP-B-6-69481, JP-A-7-97401, JP-A-7-59303). Further, production of a photo-crosslinked HA gel by irradiation of a photo-crosslinkable HA derivative is also known (JP-A-143604).

However, these cross-linked products of HA are not what is called HA any longer, and among the desired properties for materials used in vivo, non-toxicity and non-immunogenicity can not absolutely be secured for them considering procedures for removal of crosslinkers and the difficulty of complete denial of the presence of residual crosslinkers.

The present inventors have found out a simple method of producing a hardly water soluble HA gel made of hyaluronic acid alone for the first time (PCT/JP98/03536). However, the gel is sheet-like, filmy, flaky, spongy or massive and lacks fluidity.

Therefore, the present inventors have proposed a HA gel slurry obtained by suspending granules or flakes of the hardly water soluble HA gel in aqueous solution with an idea that a hardly water soluble HA-containing material with fluidity would be useful and find various medical applications. The HA gel slurry has fluidity and is easy to eject from an injector including it.

DISCLOSURE OF THE INVENTION

To take the advantages of the excellent biocompatibility which HA inherently has by itself to the maximum, hardly water soluble HA gels with fluidity obtainable without using any chemical crosslinker or modifier are favorable. But such gels have not been developed yet, and only a HA gel slurry obtained by suspending the hardly water soluble HA gel flakes in aqueous solution has been proposed.

Besides, there is a problem that the necessity to crush the hardly water soluble HA gel by using ultrasonic waves or a mixer in preparation of the HA gel adds up the production steps.

In general, transparency is also desired in view of quality control. On the other hand, for use of HA gels in the field of ophthalmology, especially as artificial vitreous bodies, fluidity is required in view of handling properties, while transparency is required in view of effectiveness. Further, gels with refractive indices closer to that of the vitreous body are preferable (1.3345–1.3348; (Ganka Shinryo Practice, Vol.22, pp234, 1996, Bunkodo, Tokyo). However, no gels have been developed yet that have these properties.

The present inventors thought that a hardly water soluble and transparent HA gel would be obtained by imparting fluidity of HA solution to a hardly water soluble HA gel made of HA alone obtained without using any crosslinker or the like and broaden the applications of HA gels and as a result of extensive research for such a gel, have accomplished the present invention.

Namely, the present invention provides (1) a gel made of HA alone which is hardly soluble in a neutral aqueous solution and has fluidity enough to be easily ejectable from an injector, (2) the HA gel according to (1), which dissolves in a neutral aqueous solution at 37° C. in 12 hours to a degree of dissolution of at most 50%, (3) the HA gel according to (1), which dissolves to yield solubilized HA having a branched structure and partly containing a molecular weight fraction with a branching degree of at least 0.5, when treated under accelerating conditions for acid hydrolysis of HA, (4) the HA gel according to any one of (1) to (3), which is transparent, (5) a method of producing the HA gel according to (4), which comprises adjusting a HA aqueous solution containing an inorganic salt to pH 3.5 or below, and freezing and thawing the solution, (6) a biomedical material containing a gel made of HA alone which satisfies the following requirements (a) and (b): (a) the HA gel dissolves in a neutral aqueous solution at 37° C. in 12 hours to a degree of dissolution of at most 50%, and (b) the gel dissolves to yield solubilized HA having a branched structure and partly containing a molecular weight fraction with a branching degree of at least 0.5, when treated under accelerating conditions for acid hydrolysis of HA, (7) a biomedical material containing a HA gel and un-gelled HA, wherein the HA gel dissolves in a neutral aqueous solution at 37° C. in 12 hours to a degree of at most 50%, and the HA gel dissolves to yield solubilized HA having a branched structure and partly containing a molecular weight fraction with a branching degree of at least 0.5, when treated under accelerating conditions for acid hydrolysis of HA, (8) the biomedical material according to (6) or (7), which is an injection for treatment of arthrosis, (9) the biomedical material according to (6) or (7), which is an embolizing material, (10) the biomedical material according to (6) or (7), which is an injection for a soft tissue, and (11) the biomedical material according to (6) or (7), which is an artificial vitreous body.

BEST MODE FOR CARRYING OUT THE INVENTION

Now, the present invention will be described below in detail.

In the present invention, HA obtained by extraction from animal tissues or by fermentation may be used without any restriction on its source.

The strain used in fermentation is preferably a HA-producing microorganism isolated from nature such as the genus Streptococcus or a mutant which steadily produces HA in high yield such as *Streptococcus equi* FM-100 (accession number 9027 given by National Institute of Bioscience and Human-Technology) disclosed in JP-A-63-123392 or *Streptococcus equi* FM-300 (accession number 2319 given by National Institute of Bioscience and Human-Technology) disclosed in JP-A-2-234689. Pure HA obtained from cultures of the above-mentioned mutants may be used.

The molecular weight of the HA to be used in the present invention is preferably within the range of from about $1\times10^5$ to about $1\times10^7$ Da. HA having a higher molecular weight may also be used after the molecular weight is lowered into this range by treatment such as hydrolysis.

In the present invention, the concept of HA is used so as to include its alkali metal salts such as sodium, potassium and lithium salts, too.

In the present invention, by HA alone, it is meant that no chemical crosslinker or chemical modifier is used other than HA, that HA is not in the form of a complex with a cationic polymer, and that the gel is an auto-crosslinked gel.

The HA gel according to the present invention is a polymer having a three dimensional network structure or its swollen product. The three dimensional network structure is made of crosslinked HA.

In the present invention, the difficulty in dissolution is defined by the solubility in a neutral aqueous solution at 37° C. and means that the gel dissolves in a neutral aqueous solution at 37° C. in 12 hours to a degree of dissolution of at most 50%, preferably at most 30%, particularly preferably at most 10%.

The HA gel according to the present invention can be solubilized through degradation by treatment under accelerating conditions for acid hydrolysis of HA. When the solubilized HA retains the crosslinked structure, it is distinguished as branched HA from linear HA according to the theory of polymer solution.

The accelerating conditions for acid hydrolysis of HA according to the present invention are preferably such that the pH of the aqueous solution is 1.5 and the temperature is 60° C. It is well known that cleavage of the main chain of HA through hydrolysis of glycosidic bonds is remarkably accelerated in an acidic or alkaline aqueous solution as compared with that in a neutral aqueous solution. In addition, acid hydrolysis is accelerated at a higher temperature.

In the present invention, the molecular weights and branching degrees of the fractions separated by GPC according to molecular weight are measured on-line continuously by the GPC-MALLS method. In the present invention, the branching degree was measured by the elution volume method which compares the molecular weight of each fraction of the solubilized HA with the molecular weight of a fraction at the same elution volume of linear HA as a control. The branching degree is the number of branch points in one polymer chain of the solubilized HA and plotted against the molecular weight of the solubilized HA. Measurement of the branching degree by the GPC-MALLS method by the elution volume method is described in PCT/JP98/03536.

Solubilized HA was diluted with the GPC eluent for concentration adjustment and filtered through a membrane filter of 0.2 µm before measurement.

If the HA gel according to the present invention has a crosslinked structure which is stable under accelerating conditions for acid hydrolysis of HA, a branched structure is recognized in the solubilized HA according to the theory of polymer solution. The HA gel according to the present invention has a branching degree of at least 0.5.

In the present invention, by easily ejectable from an injector, it is meant that the HA gel of the present invention can be ejected at room temperature about 25° C. at a rate of 0.1 ml/sec with a force of at most 50 N when loaded into a disposable syringe (hereinafter referred to as an injector) of 2.5 to 3 ml with an inner diameter of about 1 cm equipped with a disposable injection needle of 21 G with an outer diameter of about 0.8 mm.

In the present invention, transparency means that the visible light transmittance of the HA gel of the present invention in a spectrometric cuvette of 10 mm thick measured at 340 nm to 800 nm is at least 50%, preferably 70%, particularly preferably 90%, based on the transmittance of water.

For pH adjustment of a HA aqueous solution, any acid that can adjust the pH to 3.5 or below may be used. Preferably, a strong acid such as hydrochloric acid, nitric acid and sulfuric acid is used to decrease the amount of an acid.

As the inorganic salt to be added to a HA solution in the present invention, a salt of a monovalent metal such as a sodium salt or a potassium salt, or a salt of a bivalent metal such as a magnesium salt, a calcium salt or a manganese salt may be used. The metal salt to be used is preferably soluble in water at pH 3.5 or below.

The metal salt can take various forms such as a chloride, a sulfate or a nitride, when used. The concentration of the inorganic salt to be added is from 0.1 to 10 wt %, preferably from 0.2 to 2.0 wt %.

It is not favorable for preparation of a HA gel with fluidity that the concentration is below 0.1 wt %, because the resulting gel tends to be solid. It is not favorable that the concentration is over 10 wt %, because gelation takes an impractically long time.

The pH of a HA aqueous solution is adjusted so that a sufficient proportion of the carboxylic groups in HA undergoes protonation. In the present invention, it is necessary to adjust the pH to 3.5 or below, preferably to 2.5 or below, although the final pH is set depending on various factors such as the type of the counterinon in the HA salt, the molecular weight of HA, the concentration of the aqueous solution, conditions of freezing and thawing and the properties of the resulting gel such as strength.

With respect to freezing-thawing, a procedure comprising freezing the prepared acidic HA aqueous solution in an appropriate vessel at a predetermined temperature and then thawing it at a predetermined temperature is carried out at least once.

Although the freezing and thawing temperatures and times may be appropriately set depending on various factors such as the size of the vessel, the volume of the aqueous solution, the molecular weight of HA, the concentration of the aqueous solution, the pH of the aqueous solution and the concentration and kind of the metal salt in it so that the acidic HA solution freezes and thaws, it is generally preferred that the freezing temperature is not higher than the ice point, and the thawing temperature is not lower than the ice point.

It is particularly preferred that the freezing temperature is −5° C. or below, and the thawing temperature is 5° C. or above, to shorten the freezing and thawing times. There is no restriction on the freezing and thawing times so long as they are longer than it takes to complete freezing and thawing at the temperatures.

The number of times the procedure comprising freezing and then thawing the prepared acidic HA aqueous solution is repeated, depends on various factors such as the molecular weight of HA to be used, the concentration of the metal salt in it, the concentration and pH of the aqueous solution, the freezing and thawing temperatures and times and the properties of the resulting gel such as strength. Usually, it is preferred to repeat the procedure at least once.

Further, the freezing and thawing temperatures and times may be changed every time the freezing-thawing is repeated.

From the HA gel obtained by freezing and thawing a prepared acidic HA aqueous solution, the acid component added for the acidification has to be removed in order to prevent acid hydrolysis of HA. For removal of the acid component, the gel is usually washed with or dialyzed against an aqueous solvent, for example, water, physiological saline or a phosphate buffer, preferably physiological saline or a phosphate buffer. There is no restriction on the aqueous solvent so long as it does not functionally impair the HA gel.

Although there is no particular restriction on the method for washing or dialysis, dialysis is preferable. Dialysis is accomplished preferably by using a dialysis membrane or a ultrafilter. The dialysis conditions, inclusive of the volume of the solvent and the number of times of dialysis, are determined so that the concentration of the component to remove can be lowered to the desired level or below. The pH pf the dialyzed gel is adjusted to meet the purpose before use.

The HA gel of the present invention is obtainable endotoxin-free and aseptically if care is taken over the reagents, water, the vessels.

The HA gel thus prepared has fluidity by itself and is obtained with uniformity and transparency but without turbidity. It may be filled into a syringe or a bag before use. If pharmaceutically or physiologically active substances are added at the time of gelation, the resulting fluid HA gel contains these substances in it.

For example, addition of thrombin which coagulates blood by catalyzing conversion of fibrinogen into fibrin in the blood coagulation cascade with a view to accelerating embolization and addition of various antitumor agents with a view to obstructing tumor arteries may be mentioned without any restriction.

The HA gel of the present invention shows great improvement in in vivo residency and persistency over HA solution and excellently safe and biocompatible by virtue of the absence of crosslinkers. Therefore, it can be used as a biomedical material such as an injection for treatment of arthrosis, an embolizing material, an injection for a soft tissue and an artificial vitreous body.

Now, the present invention will be described in further detail with reference to Examples. However, the present invention is by no means restricted to these specific Examples.

The injectors mentioned below consisted of 2.5 to 3 ml disposable syringes with an inner diameter of about 1 cm and disposable injection needles of 21G with an outer diameter of about 0.8 mm. In the present invention, 2.5 ml syringes (with pistons having a diameter of about 12 mm) manufactured by Terumo Corporation were used together with injection needles of 21G manufactured by Terumo Corporation.

EXAMPLE 1

The sodium salt of HA (molecular weight calculated from limiting viscosity: $2 \times 10^6$ Da) was dissolved in 1.0 wt % sodium chloride solution to give a 1.0 wt % HA aqueous solution. The aqueous solution was adjusted to pH 1.5 with 1N nitric acid to give an acidic HA aqueous solution.

A 50 ml portion of the acidic HA aqueous solution was put in a metal container and placed in a refrigerator set at −20° C. After 120 hours, it was taken outside and then thawed at 25° C. to give a fluid HA gel.

Subsequently, it was dialyzed against distilled water sufficiently for removal of excess acid and sodium chloride. Then, it was dialyzed against buffered physiological saline containing 25 mM phosphate, pH 7 sufficiently for neutralization. The HA gel filled into an injector was easy to eject through the injection needle at room temperature about 25° C.

EXAMPLE 2

The sodium salt of HA (molecular weight calculated from limiting viscosity: $2 \times 10^6$ Da) was dissolved in 0.5 wt % sodium chloride solution to give a 0.5 wt % HA aqueous solution. The aqueous solution was adjusted to pH 1.5 with 1N nitric acid to give an acidic HA aqueous solution.

A 50 ml portion of the acidic HA aqueous solution was put in a metal container and placed in a refrigerator set at −20° C. After 50 hours, it was taken outside and then thawed at 25° C. to give a fluid HA gel.

Subsequently, it was dialyzed against distilled water sufficiently for removal of excess acid and sodium chloride. Then, it was dialyzed against buffered physiological saline containing 25 mM phosphate, pH 7 sufficiently for neutralization. The HA gel filled into an injector was easy to eject through the injection needle at room temperature about 25° C.

EXAMPLE 3

The sodium salt of HA (molecular weight calculated from limiting viscosity: $2 \times 10^6$ Da) was dissolved in 1.0 wt % magnesium chloride solution to give a 1.0 wt % HA aqueous solution. The aqueous solution was adjusted to pH 1.5 with 1N nitric acid to give an acidic HA aqueous solution.

A 50 ml portion of the acidic HA aqueous solution was put in a metal container and placed in a refrigerator set at −20° C. After 120 hours, it was taken outside and then thawed at 25° C. to give a fluid HA gel.

Subsequently, it was dialyzed against distilled water sufficiently for removal of excess acid and magnesium chloride. Then, it was dialyzed against buffered physiological saline containing 25 mM phosphate, pH 7 sufficiently for neutralization. The HA gel filled into an injector was easy to eject through the injection needle at room temperature about 25° C.

EXAMPLE 4

Preparation of Thrombin-containing Fluid HA Gel

To the fluid HA gel obtained in Example 2, thrombin in solution was added in an amount of 0.5 NIH unit per 100 mg to obtain a thrombin-containing fluid HA gel.

COMPARATIVE EXAMPLE 1

(Freeze-dried HA)

A 1.0 wt % HA solution obtained in Example 1 was frozen and thawed under the same conditions as in Example 1 without pH adjustment, but gelation did not happen. The solution was freeze-dried for use in a solubility test as a control.

REFERENCE EXAMPLE 1

(HA Gel Slurry)

The sodium salt of HA (molecular weight calculated from limiting viscosity: $2 \times 10^6$ Da) was dissolved in distilled water to give a 1.0 wt % HA aqueous solution. The aqueous solution was adjusted to pH 1.5 with 1N nitric acid to give an acidic HA aqueous solution.

A 50 ml portion of the acidic HA aqueous solution was put in a metal container and placed in a refrigerator set at −20° C. After 120 hours, it was taken outside and then thawed at 25° C. to give a HA gel.

Subsequently, it was dialyzed against distilled water sufficiently for removal of excess acid and sodium chloride. Then, it was dialyzed against buffered physiological saline containing 25 mM phosphate, pH 7 sufficiently for neutralization and then sufficiently dialyzed against distilled water again to give a sheet of a HA gel.

100 mg of the HA gel was put in 10 ml buffered physiological saline containing 25 mM phosphate and crashed with a microhomogenizer (Polytoron, manufactured by Kinematica AG) to give a HA gel slurry. The HA gel slurry was used for a transparency test. The HA gel slurry filled into an injector was easy to eject through the injection needle at room temperature about 25° C.

EXAMPLE 4

Test by Ejection From Injector

HA gels of the present invention were filled into 2.5 ml syringes (with pistons having a diameter of about 12 mm) manufactured by Terumo Corporation equipped with injection needles of 21G manufactured by Terumo Corporation, and the forces required to eject them at a rate of 0.1 ml/sec were measured by means of Tensilon EZ Test-20N manufactured by Shimadzu Corporation. The results are shown below in Table 1.

As a control, a 1 wt % HA aqueous solution in phosphate buffered physiological saline. 1 wt % HA solution has been already used as a drug for joints like Altz manufactured by Seikagaku Corporation.

TABLE 1

| | Comparison of ejection forces | | |
|---|---|---|---|
| Experiment No. | Sample | Ejection force (N) | Remarks |
| 3 | Fluid HA gel of Example 1 | 10.5 | Example |
| 2 | Fluid HA gel of Example 2 | 8.5 | Example |
| 3 | Fluid HA gel of Example 3 | 11.0 | Example |
| 4 | 1 wt % HA solution | 5.1 | Comparative Example | from Table 1, it is evident that the fluid HA gels obtained are easily ejectable from an injector.

EXAMPLE 5

Solubility Test

A phosphate buffer was added to physiological saline at a concentration of 50 mM to give a phosphate buffer-physiological saline at pH 7.0. the fluid HA gels obtained in Examples 1 to 3 and the freeze-dried HA obtained in comparative Example 1 were weighed out, 100 mg each on the dry basis and immersed in 50 ml of the phosphate buffer-physiological saline with stirring at 37° C. while sampled at intervals. The HA dissolved in phosphate buffer-physiological saline was determined by the carbazole-sulfate method, and the degrees of dissolution were calculated. The results were shown below in Table 2.

TABLE 2

Comparison of solubilities

| Experiment No. | Sample | Degree of dissolution (%) | | | | Remarks |
|---|---|---|---|---|---|---|
| | | After 12 hours | After 7 days | After 14 days | After 30 days | |
| 5 | Fluid HA gel of Example 1 | 2 | 7 | 13 | 21 | Example |
| 6 | Fluid HA gel of Example | 2 | 10 | 21 | 49 | Example |
| 7 | Fluid HA gel of Example | 2 | 8 | 15 | 26 | Example |
| 8 | Freeze-dried HA of Comparative Example 1 | 100 | — | — | — | Comparative Example |

As is evident from Table 2, the fluid HA gels were hardly soluble while the control was easy to dissolve.

EXAMPLE 6

Measurement of Branching Degree

The HA gels obtained in Examples 1 to 3 were hydrolyzed in 15 ml of aqueous hydrochloric acid pH 1.5 at 60° C. for 6 hours to complete volatilization. The solubilized gels were diluted by a factor of 2 with the GPC eluent to 0.05 wt % and filtered through a membrane filter of 0.2 $\mu$m, and 0.1 ml portions of them were injected for GPC-MALLS measurement. The branching degrees of all the samples were 0.5 or above.

EXAMPLE 7

Transparency Test

The fluid HA gels obtained in Examples 1 to 3 and the HA gel slurry obtained in Reference Example 1 were filled into spectrometric cuvettes of 10 mm thick, and the transmittances against visible light of from 340 nm to 800 nm based on the transmittance of water were measured by means of Beckman spectrophotometer DU-64. The results are shown in Table 3. As a the control, a wt % HA aqueous solution in phosphate buffere-physiological saline was used.

TABLE 3

Transparency test

| Experiment No. | Sample | Transmittance (%) (min to max) | Remarks |
|---|---|---|---|
| 9 | Fluid HA gel of Example 1 | 92 to 95 | Example |
| 10 | Fluid HA gel of Example 2 | 95 to 98 | Example |
| 11 | Fluid HA gel of Example 3 | 93 to 95 | Example |
| 12 | HA gel slurry of Reference Example 1 | 6 to 8 | Reference Example |
| 13 | 1 wt % HA solution | 99 to 100 | Control |

From Table 3, it is evident that the fluid HA gels obtained in Examples 1 to 3 were transparent.

EXAMPLE 8

Comparison of Retention in Rabbit Articular Cavity

Both knees of male adult normal New Zealand White rabbits weighing 2.5 to 3.0 kg were shorn with an electric clipper and disinfected. 1% aqueous solution of the fluid HA gel obtained in Example 1 or HA (molecular weight calculated from limiting viscosity: $2 \times 10^6$ Da) in physiological saline was administered into the left knee articular cavities at a dose of 0.1 ml/kg weight, and physiological saline was administered into the right knee articular cavities at a dose of 0.1 ml/kg weight as a control. After the administration, synovial fluid was taken from both knees every two days, and the HA concentrations of the synovial fluid samples were determined by GPC.

The persistence was calculated from the following equation wherein the intrinsic HA is the HA content of the synovial fluid sample taken from a articular cavity immediately after administration of physiological saline.

Persistence (%)=(Recovery−Intrinsic HA content)/dosage×100

The results are shown in Table 4.

TABLE 4

Comparison of retention

| | | HA persistence (%) mean: n = 3 | | | | | | | |
|---|---|---|---|---|---|---|---|---|---|
| Experiment No. | Sample | 2 days | 4 days | 6 days | 8 days | 10 days | 12 days | 14 days | Remarks |
| 14 | Fluid HA gel of Example 1 | 90 | 68 | 30 | 11 | 5 | 1 | 0 | Example |

TABLE 4-continued

Comparison of retention

| | | HA persistence (%) mean: n = 3 | | | | | | | |
|---|---|---|---|---|---|---|---|---|---|
| Experiment No. | Sample | 2 days | 4 days | 6 days | 8 days | 10 days | 12 days | 14 days | Remarks |
| 15 | 1 wt % HA solution | 42 | 5 | 0 | NT | NT | NT | NT | Comparative Example |

(Note) NT denotes not tested.

From Table 4, it is evident that the fluid HA gel has much better in vivo persistence than the HA solution.

EXAMPLE 9

Bradykinin-induced Pain Suppression Effect

Into the hind limb knee articular cavities of female beagles weighing about 10 kg, the fluid HA gel obtained in Example 2 (0.3 ml/kg body mass), a 1% HA aqueous solution in physiological saline (molecular weight calculated from limiting viscosity: $2 \times 10^6$ Da, 0.3 ml/kg body mass) or physiological saline as a control (0.3 ml/kg body mass) was administered first, and 2, 4 and 7 days after administration, an aqueous solution of bradykinin, a pain-producing substance, in physiological saline (BK: 0.2 μg/ml, 0.05 ml/kg body mass) was administered. The pain suppression effect was determined on the basis of the body mass proportion loaded on a limb suffering pain between 1 and 2 minutes, 3 and 4 minutes and 5 and 6 minutes after. The results are shown in Table 5. The body mass proportion is represented by the following equation.

TABLE 5

Comparison of pain suppression effect

| Experiment No. | Sample | Body mass proportion (%) mean: n = 10 | | | Remarks |
|---|---|---|---|---|---|
| | | After 2 days | After 4 days | After 7 days | |
| 16 | Fluid HA gel of Example 2 | 74 | 72 | 53 | Example |
| 17 | 1 wt % HA solution | 61 | 37 | 28 | Comparative Example |
| 18 | Control (physiological saline) | 27 | 25 | 29 | Comparative Example |

Body mass proportion (%) =

$$\frac{\text{(Mean body mass proportion loaded on a subject limb at a predetermined time after BK administration)}}{\text{(Mean body mass proportion loaded on a subject limb for 1 minute period before BK administration)}} \times 100$$

From Table 5, it is evident that the fluid HA gels maintained its pain suppression effect even after 7 days while the suppression effects of the HA solution diminished to the same level as the control in 7 days.

EXAMPLE 10

Blood Coagulation Test

Human whole blood mixed with the fluid HA gel obtained in Example 1 coagulated under heating at 37° C. in 5 minutes.

On the other hand, human blood mixed with the thrombin-containing fluid HA gel obtained in Example 4 underwent apparent coagulation under heating at 37° C. in 2 minutes.

EXAMPLE 11

Embolization Test

The thrombin-containing fluid HA gel obtained in Example 4 was sucked into an injector and intra-arterially administered into the auricles of New Zealand White rabbits weighing about 2.5 kg at a dose of about 0.1 ml. The injected gel quickly coagulated, developing visible recognizable obstruction.

No change was not seen during 1 month in morphological observation, and a histological postmortem examination of the emboli revealed satisfactory obstruction.

EXAMPLE 12

Administration Test on Guinea Pigs 0.5 wt % aqueous solutions of the fluid HA gels obtained in Examples 1 to 3 and the sodium salt of HA (molecular weight calculated from limiting viscosity: $2 \times 10^6$) in physiological saline were hypodermically administered into twenty female Hartray guinea pigs weighing 350 to 400 g under anaesthesia at a dose of 0.05 ml, 10 sites per individual. 0, 1, 2, 3 and 4 weeks after, the tissues of the respective sites were sampled from one of each administration group. They were sectioned after fixation and embedding, and the sections were stained with hematoxylin-eosin and Alcian Blue and histologically examined under a microscope.

The results indicate that when the samples obtained in Examples 1 to 3 were administered, the skin maintained in the same state as immediately after the administration HA and contained HA in the tissue even after 4 weeks, while 0.5 wt % HA aqueous solution in physiological saline was absorbed completely in 4 weeks. No exudation from cells that suggests inflammatory reactions was observed.

EXAMPLE 13

Refractive Index Measurement

The refractive indices of the fluid HA gels obtained in Example 1 and 2 at 20° C. were measured by means of Abbe refractometer (manufactured by Atago) and found to be similar to that of the vitreous body, 1.335 and 1.334, respectively.

EXAMPLE 14

Effect on Rabbit Retinal Detachment

Fifteen white rabbits (New Zealand White) weighing from 2.5 to 3.0 kg were (15 eyes) were subjected to retrobulbar anaesthetization with 2% lidocaine hydrochloride following induction of mydriasis by instillation of 0.5% indomethacin and 5% phenylephrine hydrochloride.

After eye washing and periocular disinfection, a rabbit was anchored under a surgical microscope. After bridle suture, the conjunctiva was incised. The sclera was incised, and a perfusion tap was fixed inside with a prosuspensor. The sclera was incised further for insertion of a vitreous adenotome and a light guide, and a vitreous adenotome and a light guide were inserted.

After vitrectomy with the vitreous adenotome under suction, a needle of 21G with a curved tip was inserted instead of the vitreous adenotome. The needle of 21G was inserted on the epiotic side of the retina, and about 0.1 ml of sterilized air was introduced to below the retina to partly detach the retina. After the detachment, a vitreous adenotome was inserted again to form a slit by partial incision on the peeled retina.

After replacement of the persulate with air, a fluid HA gel obtained in Example 1 or 2 was injected into the vitreous cavity to bring back the retina through replacement of the air.

The probe of a laser beam intraocular photocoagulator was inserted into the vitreous cavity for intraocular coagulation, and the scleral incision was closed with a 80 nylon suture.

The results of microscopic analysis after 4 weeks revealed that the fluid gels obtained in Examples 1 and 2 induced no abnormal symptoms such as reccurent retinal detachment and the photocoagulated site cicatrized satisfactorily. Neither vitreous clouding nor inflammatory reactions were not observed under a slit lump.

INDUSTRIAL APPLICABILITY

The present invention provides a hardly water soluble HA gel made of hyaluronic acid alone with fluidity or with fluidity and transparency. The HA gel according to the present invention retains the structure of the biologically inherent HA by virtue of obviation of use of crosslinkers, and is excellently safe and biocompatible. It is advantageous in quality control for its transparency.

Therefore, it is useful as a biomedical material such as an injection for treatment of arthrosis, an embolizing material, an injection for a soft tissue and an artificial vitreous body.

What is claimed is:

1. A hyaluronic acid gel, comprising water and hyaluronic acid, wherein said hyaluronic acid is not in the form of a complex with a cationic polymer and wherein the hyaluronic acid gel is autocrosslinked, hardly soluble in a neutral aqueous solution, and has fluidity enough to be easily ejectable from an injector, and wherein said hyaluronic acid gel dissolves to yield solubilized hyaluronic acid having a branched structure and comprising a molecular weight fraction with a branching degree of at least 0.5, when treated under accelerating conditions for acid hydrolysis of hyaluronic acid.

2. The hyaluronic acid gel according to claim 1, wherein said hyaluronic acid gel dissolves in a neutral aqueous solution at 37° C. in 12 hours to a degree of dissolution of at most 50%.

3. The hyaluronic acid gel according to claim 1, which is transparent.

4. A method of producing the hyaluronic acid gel according to claim 1, which comprises adjusting a hyaluronic acid aqueous solution containing an inorganic salt to pH 3.5 or below, and freezing and thawing he solution.

5. A biomedical material comprising a hyaluronic acid gel which satisfies the following requirements (a)–(c):

(a) the hyaluronic acid gel dissolves in a neutral aqueous solution at 37° C. in 12 hours to a degree of dissolution of at most 50%, (b) the hyaluronic acid gel dissolves to yield solubilized hyaluronic acid having a branched structure and containing a molecular weight fraction with a branching degree of at least 0.5, when treated under accelerating conditions for acid hydrolysis of hyaluronic acid, and (c) the hyaluronic acid gel is autocrosslinked.

6. A biomedical material comprising an autocrosslinked hyaluronic acid gel and un-gelled hyaluronic acid, wherein the hyaluronic acid gel dissolves in a neutral aqueous solution at 37° C. in 12 hours to a degree of at most 50%, and the hyaluronic acid gel dissolves to yield solubilized hyaluronic acid having a branched structure and containing a molecular weight fraction with a branching degree of at least 0.5, when treated under accelerating conditions for acid hydrolysis of hyaluronic acid.

7. The biomedical material according to claim 5, which is an injection for treatment of arthrosis.

8. The biomedical material according to claim 5, which is an embolizing material.

9. The biomedical material according to claim 5, which is an injection for a soft tissue.

10. The biomedical material according to claim 5, which is an artificial vitreous body.

11. The biomedical material according to claim 6, which is an injection for treatment of arthrosis.

12. The biomedical material according to claim 6, which is an embolizing material.

13. The biomedical material according to claim 6, which is an injection for a soft tissue.

14. The biomedical material according to claim 6, which is an artificial vitreous body.

15. The hyaluronic acid gel according to claim 1, wherein the hyaluronic acid gel is ejectable at room temperature at a rate of 0.1 ml/sec with a force of at most 50 N when loaded into a 2.5 to 3 ml injector having an inner diameter of about I cm equipped and having a injection needle of 21 G with an outer diameter of about 0.8 mm.

16. The hyaluronic acid gel according to claim 2, wherein the hyaluronic acid gel is ejectable at room temperature at a rate of 0.1 ml/sec with a force of at most 50 N when loaded into a 2.5 to 3 ml injector having an inner diameter of about 1 cm equipped and having a injection needle of 21 G with an outer diameter of about 0.8 mm.

\* \* \* \* \*